US012716047B2

(12) United States Patent
Morita et al.

(10) Patent No.: US 12,716,047 B2
(45) Date of Patent: Aug. 25, 2026

(54) CELL PROCESSING METHOD AND CELL PROCESSING APPARATUS

(71) Applicant: CANON KABUSHIKI KAISHA, Tokyo (JP)

(72) Inventors: Yuki Morita, Kanagawa (JP); Sachiko Yamauchi, Kanagawa (JP); Tatsuaki Orihara, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 799 days.

(21) Appl. No.: 18/062,992

(22) Filed: Dec. 7, 2022

(65) Prior Publication Data

US 2023/0183632 A1 Jun. 15, 2023

(30) Foreign Application Priority Data

Dec. 9, 2021 (JP) ................................ 2021-200173
Dec. 1, 2022 (JP) ................................ 2022-193110

(51) Int. Cl.

*C12N 15/87* (2006.01)
*B01L 3/00* (2006.01)
*C12M 1/42* (2006.01)
*C12N 13/00* (2006.01)

(52) U.S. Cl.

CPC ....... *C12M 35/04* (2013.01); *B01L 3/502761* (2013.01); *C12N 13/00* (2013.01); *C12N 15/87* (2013.01); *B01L 2200/0652* (2013.01); *B01L 2300/0681* (2013.01); *B01L 2300/087* (2013.01)

(58) Field of Classification Search

None

See application file for complete search history.

(56) References Cited

U.S. PATENT DOCUMENTS

2010/0160183 A1 6/2010 Xu et al.

FOREIGN PATENT DOCUMENTS

JP 5645657 B2 12/2014

OTHER PUBLICATIONS

Migita et al. "Cell cycle and size sorting of mammalian cells using a microfluidic device" (2010), Analytical Methods, vol. 2: 657-660. (Year: 2010).*

Jones et al. "Connections between the cell cycle, cell adhesion and the cytoskeleton", (2019) Phil. Trans. R. Soc. B, 374: 1'-10. (Year: 2019).*

* cited by examiner

*Primary Examiner* — Teresa E Knight

(74) *Attorney, Agent, or Firm* — Canon U.S.A., Inc., IP Division

(57) ABSTRACT

Provided is a cell processing method including: preparing a cell suspension containing a cell to be processed and a target substance; and introducing the target substance into the cell to be processed by allowing a shear force to act on the cell to be processed, wherein the cell to be processed is a cell, which is selected from a cell group including cells in a proliferation process, and which has a cell diameter larger than a mode in a cell diameter distribution of the cell group.

7 Claims, 7 Drawing Sheets

CELL PROCESSING METHOD AND CELL PROCESSING APPARATUS

PRIORITY AND INCORPORATION BY REFERENCE

This application claims the benefit of Japanese Patent Application No. 2021-200173, filed Dec. 9, 2021 and Japanese Patent Application No. 2022-193110, filed Dec. 1, 2022, which are hereby incorporated by reference herein in their entirety.

BACKGROUND OF THE DISCLOSURE

Field of the Disclosure

The present disclosure relates to a cell processing method and a cell processing apparatus.

Description of the Related Art

In recent years, with the advent of induced pluripotent stem cells and cell therapeutics, which are obtained by modifying properties of cells, a technology for introducing a target substance typified by a nucleic acid into a living cell has been attracting attention. As a method generally used in such technology, there are known a chemical method involving using a cationic substance with respect to a living cell and a biological method involving using a virus with respect thereto. Other existing methods include: physical methods, such as an electroporation method and a gene gun method, each of which is expected to achieve low toxicity; and a microinjection method, which has high selectivity for a target substance species, thereby enabling its introduction with high reliability, and various methods are being developed.

With regard to a physical method for introducing a target substance into a living cell, in Japanese Patent No. 5645657, as a cell processing method including a step of passing a liquid containing a cell through an orifice, there is a description of an introduction method involving using an inkjet device used as an image recording apparatus. The target substance of interest can be introduced into a cell by generating a pressure and a shear force in a micro-sized space in the inkjet device. The method described in Japanese Patent No. 5645657 had room for improvement in efficiency of the introduction of the target substance into the cell. In addition, in Japanese Patent No. 5645657, there is a description of a technique for improving the introduction efficiency by setting conditions for utilization of the target substance. However, the target substance to be introduced is itself limited as a consequence, and hence there was a problem from the viewpoint of versatility.

SUMMARY OF THE DISCLOSURE

The present disclosure is directed to provide a cell processing method and a cell processing apparatus being highly versatile for usable target substances and highly efficient for introducing a target substance into a cell.

The above-mentioned object is achieved by the present disclosure described below.

That is, according to one aspect of the present disclosure, there is provided a cell processing method including: a preparing step of preparing a cell suspension containing a cell to be processed and a target substance; and an introducing step of introducing the target substance into the cell to be processed by allowing a shear force to act on the cell to be processed, wherein the cell to be processed is a cell, which is selected from a cell group including cells in a proliferation process, and which has a cell diameter larger than a mode in a cell diameter distribution of the cell group.

In addition, according to another aspect of the present disclosure, there is provided a cell processing apparatus to be used for introducing a target substance into a cell to be processed, the cell processing apparatus including: a cell selecting member selecting a cell from a cell group including cells in a proliferation process as a cell to be processed, the cell to be processed having larger cell diameter than a mode in a cell diameter distribution of the cell group; and a shear force applying member applying a shear force to the cell to be processed to introduce the target substance into the cell to be processed.

In particular, the present disclosure provides a cell processing method comprising a preparing step of preparing a cell suspension containing a cell to be processed and a target substance; and an introducing step of introducing the target substance into the cell to be processed by allowing a shear force to act on the cell to be processed, wherein the cell to be processed is a cell, which is selected from a cell group including cells in a proliferation process, and which has a cell diameter larger than a mode in a cell diameter distribution of the cell group.

The present disclosure additionally provides that in the cell processing method, the cell to be processed can be a cell having a cell diameter 1.3 or more times the mode in the cell diameter distribution of the cell group. Further, the cell processing method further provides that the allowing a shear force to act can be passing the cell suspension through an orifice.

It is further provided that in the provided cell processing methods, the orifice can be included in a liquid ejection head, and the introducing step comprises ejecting the cell suspension from the orifice by the liquid ejection head. For instance, in the provided cell processing methods, the liquid ejection head includes: a plurality of the orifices arrayed in a row; a common liquid chamber having a shape extending along the row of the orifices; and a plurality of supply flow paths each configured to communicate the common liquid chamber to a corresponding one of the orifices, wherein the common liquid chamber can be configured so that a mixed liquid containing the cell group and the target substance can be supplied to each of the supply flow paths while flowing from one end side of the row of the orifices to another end side thereof, wherein a connection portion between the common liquid chamber and each of the supply flow paths has arranged therein a pillar-shaped nozzle filter, wherein the nozzle filters have a smaller pillar diameter on a downstream side of a flow of the mixed liquid in the common liquid chamber than on an upstream side thereof, and have, on a most upstream side of the flow of the mixed liquid in the common liquid chamber, a pillar diameter of such a size that the cell to be processed cannot be supplied to a corresponding one of the supply flow paths, and have, on a most downstream side of the flow of the mixed liquid in the common liquid chamber, a pillar diameter of such a size that the cell to be processed can be supplied to a corresponding one of the supply flow paths, and wherein the cell to be processed can be selected from the cell group through utilization of the nozzle filters.

Furthermore, in the provided cell processing methods the cell to be processed can be a cell selected from the cell group through a mesh filter. As a further description of the provided cell processing methods, the cell group can contain adherent cells, and the cell to be processed can be a cell selected from the cell group through utilization of a change in adherence of the adherent cells to a surface of a culture substrate in a culture process.

Yet further still, in the provided cell processing methods, the target substance can be a nucleic acid.

The present disclosure further provides a cell processing apparatus to be used for introducing a target substance into a cell to be processed, the cell processing apparatus comprising: a cell selecting member selecting a cell from a cell group including cells in a proliferation process as a cell to be processed, the cell to be processed having larger cell diameter than a mode in a cell diameter distribution of the cell group; and a shear force applying member applying a shear force to the cell to be processed to introduce the target substance into the cell to be processed. The present disclosure additionally provides that in the cell processing apparatus, the cell selecting member can be a nozzle filter. Further, it is provided that in the provided cell processing apparatuses, the shear force applying member can be an orifice forming member.

Additionally, the cell processing apparatus can comprise a plurality of orifices as the shear force applying member arrayed in a row; a common liquid chamber having a shape extending along the row of the orifices; and a plurality of supply flow paths each configured to communicate the common liquid chamber to a corresponding one of the orifices, wherein the common liquid chamber can be configured so that a mixed liquid, which contains a cell group including cells in a proliferation process, and the target substance, can be supplied to each of the supply flow paths while flowing from one end side of the row of the orifices to another end side thereof, wherein a connection portion between the common liquid chamber and each of the supply flow paths has arranged therein a pillar-shaped nozzle filter as the cell selecting member, and wherein the nozzle filters have a smaller pillar diameter on a downstream side of a flow of the mixed liquid in the common liquid chamber than on an upstream side thereof, and have, on a most upstream side of the flow of the mixed liquid in the common liquid chamber, a pillar diameter of such a size that the cell to be processed cannot be supplied to a corresponding one of the supply flow paths, and have, on a most downstream side of the flow of the mixed liquid in the common liquid chamber, a pillar diameter of such a size that the cell to be processed can be supplied to a corresponding one of the supply flow paths.

Further features of the present disclosure will become apparent from the following description of exemplary embodiments with reference to the attached drawings.

DESCRIPTION OF THE EMBODIMENTS

As an important indicator in the introduction of a target substance into a cell, there is given efficiency of the introduction of the target substance into the cell. Based on the opportunities to increase efficiency of the method described in Japanese Patent No. 5645657 above, the inventors have made extensive investigations regarding a cell processing method and a cell processing apparatus, the cell processing method and the cell processing apparatus being highly versatile for usable target substances and highly efficient for introducing a target substance into a cell. Thus, the inventors have reached the present disclosure.

A cell processing method according to the present disclosure and a cell processing apparatus according to the present disclosure are described in detail below with specific exemplification. Specific examples described below do not limit the present disclosure, and not all combinations of features described below are essential.

Figure 1A:
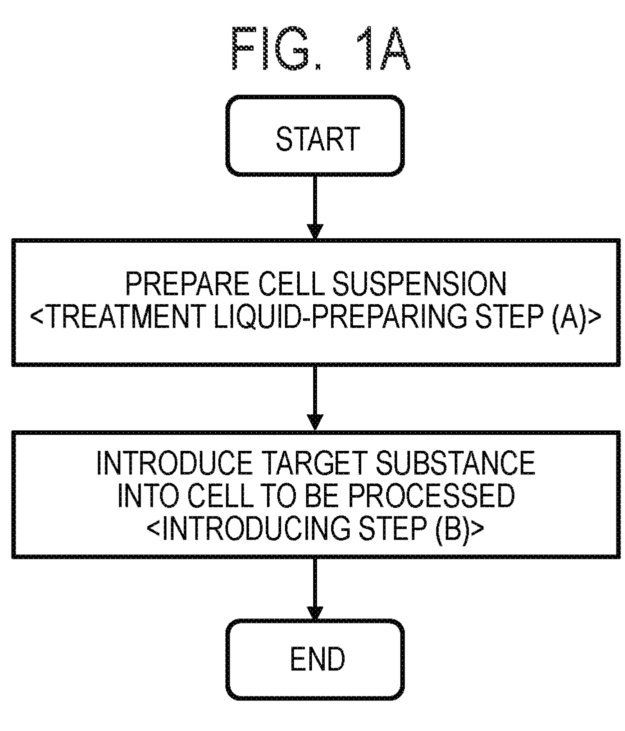
FIG. 1A is a diagram for illustrating a flowchart of a cell processing method according to one embodiment of the present disclosure.

FIG. 1A is a diagram for illustrating a flowchart of a cell processing method according to one embodiment of the present disclosure. The cell processing method according to this embodiment includes the following steps:

(A) a preparing step of preparing a cell suspension containing a cell to be processed and a target substance; and (B) an introducing step of introducing the target substance into the cell to be processed by allowing a shear force to act on the cell to be processed.

Here, the cell to be processed to be used in the preparing step (A) is a cell, which is selected from a cell group including cells in a proliferation process, and which has a cell diameter larger than the mode in the cell diameter distribution of the cell group. The cell to be processed is preferably a cell having a cell diameter 1.3 or more times the mode in the cell diameter distribution of the cell group. Cells having a cell diameter 1.3 more times the mode in the cell diameter distribution of the cell group can be identified as being in a proliferation process. The mode in the cell diameter distribution of the cell group can be determined as follows. Cell diameter of each cell is measured using an image of the cell group which recorded by using an optical microscope provided with an image sensor. Then, cells are divided into classes based on the difference in the cell diameter of 1 μm and a histogram is produced using the classes. The mode in the cell diameter distribution of the cell group is the cell diameter indicating highest frequency in the histogram. The cell suspension may also be called a cell processing liquid.

Figure 1B:
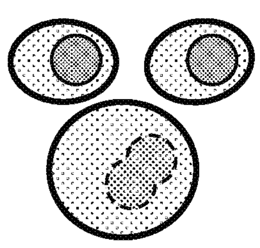
FIG. 1B is a schematic view for illustrating a cell group including cells in a proliferation process.
Figure 1C:
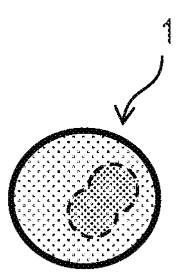
FIG. 1C is a schematic view for illustrating a cell to be processed having a cell diameter 1.3 or more times the mode in the cell diameter distribution of the cell group.

In this embodiment, such a cell group including cells in a proliferation process as illustrated in FIG. 1B is used. In the preparing step (A), such a cell 1 to be processed having a cell diameter larger than the mode in the cell diameter distribution of the above-mentioned cell group as illustrated in FIG. 1C is selected from the cell group by a cell selecting member. Subsequently, the selected cell 1 to be processed and a target substance 2 are mixed with each other in a liquid. Thus, such a cell suspension containing the cell 1 to be processed and the target substance 2 as illustrated in FIG. 1D may be prepared.

Figure 1D:
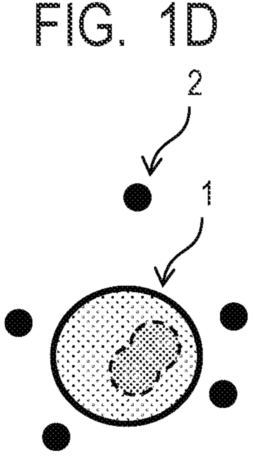
FIG. 1D is a schematic view for illustrating a cell suspension containing the cell to be processed and a target substance.
Figure 1E:
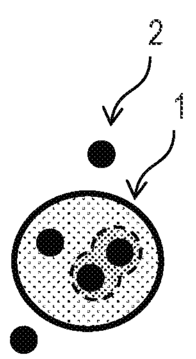
FIG. 1E is a schematic view for illustrating the cell to be processed having the target substance introduced thereinto.
Figure 1F:
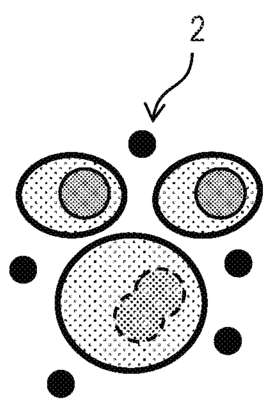
FIG. 1F is a schematic view for illustrating a mixed liquid containing the cell group and the target substance.

Alternatively, in the preparing step (A), first, as illustrated in FIG. 1F, the above-mentioned cell group and the target substance 2 are mixed with each other in a liquid to be described later to prepare a mixed liquid containing the cell group and the target substance. Subsequently, the cell 1 to be processed having a cell diameter larger than the mode in the cell diameter distribution of the cell group is selected. Thus, such cell suspension containing the cell 1 to be processed and the target substance 2 as illustrated in FIG. 1D may be prepared.

In the introducing step (B), the cell suspension illustrated in FIG. 1D, which has been prepared in the preparing step (A), is passed through an orifice, and thus, as illustrated in FIG. 1E, the target substance 2 is introduced into the cell 1 to be processed.

Figure 2A:
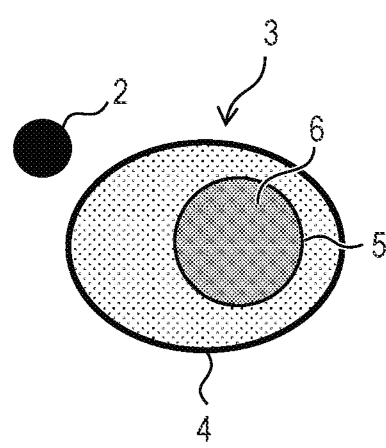
FIG. 2A is a schematic view for illustrating the state of a cell before processing.

A mechanism by which cell processing is carried out through the above-mentioned steps is described in detail with reference to FIG. 1A to FIG. 3C. FIG. 2A is a view for illustrating the state of a cell before processing. In order to carry out cell processing, the target substance 2 needs to pass through a cell membrane 4 and a nuclear membrane 5 of a cell 3 to reach a nucleus 6.

Figure 2B:
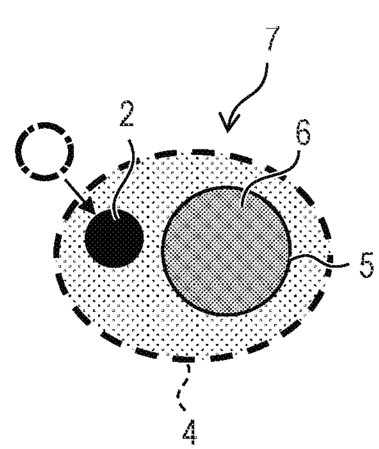
FIG. 2B is a schematic view for illustrating the passing of the target substance through a cell membrane.

In the introducing step (B) of allowing a shear force to act on the cell to be processed out of the above-mentioned steps, as illustrated in FIG. 2B, the target substance 2 passes through the cell membrane 4. In this case, the allowing a shear force to act on the cell to be processed is preferably passing the cell suspension through an orifice. It is known that, in general, when a liquid passes through an orifice, a shear force is generated because of, for example, a change in flow velocity or a difference in flow velocity depending on positions. It is considered that, when the liquid contains the cell 3, the cell 3 is subjected to a shear force from a fluid flowing around the cell 3, which punctures the cell membrane 4 to form a cell 7 having a puncture in the cell membrane 4.

Here, as a method of applying a shear force on the cell membrane 4 by a simple configuration, the method involving passing the cell 3 through an orifice has been described. However, the method of applying a shear force on the cell membrane 4 may be any other method as long as a shear force can be applied on the cell membrane 4. As an example of the method of applying a shear force on the cell membrane 4, there is given a method involving passing the cell 3 through a microchannel having a tube diameter smaller than the cell diameter to apply a shear force on the cell membrane 4 of the cell 3.

Figure 2C:
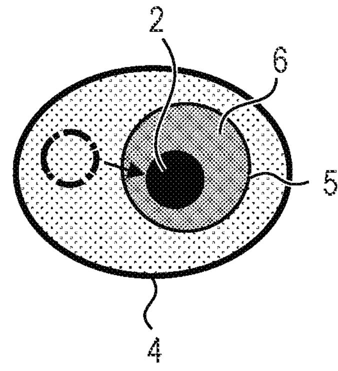
FIG. 2C is a schematic view for illustrating a process in which the target substance passes through a nuclear membrane.

In this embodiment, that the above-mentioned cell to be processed is a cell having a cell diameter larger than the mode in the cell diameter distribution of the cell group including cells in a proliferation process is effective for such a process as illustrated in FIG. 2C, in which the target substance 2 passes through the nuclear membrane 5. FIG. 2C shows a state of a cell just before the cell is divided into two cells. One cell 3 divides into two new cells to proliferate. At this time, the nucleus 6 of the cell 3 also divides to form two new nuclei. In the division process of the nucleus 6, the cell 3 lets the nuclear membrane 5 disappear.

Figure 3A:
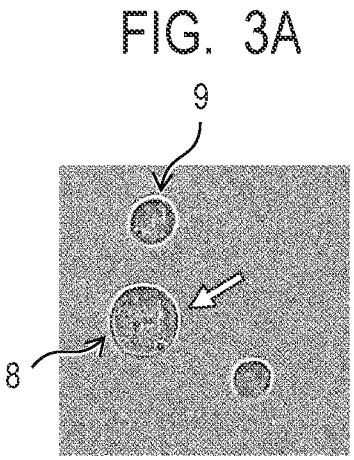
FIG. 3A shows a bright-field image capturing the appearance of cells in a cell division process.
Figure 3B:
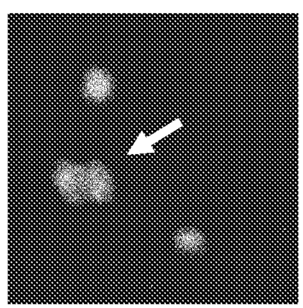
FIG. 3B shows a fluorescence image capturing the appearance of the cells in a cell division process.
Figure 3C:
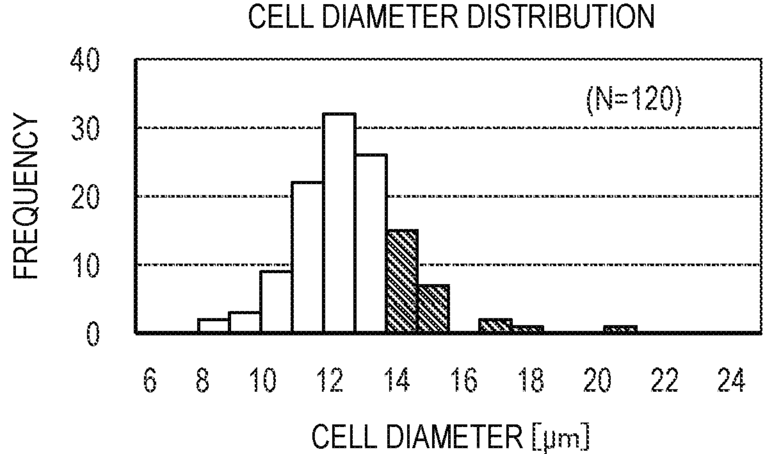
FIG. 3C is a histogram showing the cell diameter distribution of a cell group.

FIG. 3A to FIG. 3C show images capturing the appearance of cells in a division process, and a histogram of a cell diameter distribution. FIG. 3A and FIG. 3B show images obtained by observing cells in a division process with a fluorescence microscope, FIG. 3A shows a bright-field image, and FIG. 3B shows a fluorescence image obtained by staining nuclei with a fluorescent dye. The bright-field image shown in FIG. 3A and the fluorescence image shown in FIG. 3B are images taken in the same field of view.

In FIG. 3A and FIG. 3B, a cell 8 in a division process indicated by the arrow has one nucleus, which is constricted, having its appearance captured in the middle of dividing into two. The cell 8 in a division process has a large cell diameter as compared to another cell 9 not in a division process.

The results of actual measurement of cell diameters for cells in a cell group including both of the cell 8 in a division process and the cell 9 not in a division process (number of trials n=120) are shown in FIG. 3C. The histogram shown in FIG. 3C is one prepared with classes at intervals of 1 μm. Further, in the histogram shown in FIG. 3C, classes each including one or more cells having the appearance of the nucleus captured in the middle of dividing into two are represented by hatched bars.

It may be recognized from the histogram shown in FIG. 3C that the cell diameters of the cells in a division process are included in classes having relatively large cell diameters. That is, when the cells to be used for processing are set to be cells having large cell diameters, the ratio at which cells in a division process serve as processing targets can be increased. In the cells in a nuclear division process, the nuclear membrane 5 has disappeared, and hence, in the process illustrated in FIG. 2C, in which the target substance 2 passes through the nuclear membrane 5, the target substance 2 having passed through the cell membrane 4 can reach the inside of the nucleus 6 without being influenced by the nuclear membrane 5. Accordingly, when the ratio at which the cells in a nuclear division process (a cell proliferation process) serve as processing targets is increased, the efficiency of the introduction of the target substance 2 into the cell 3 in the processing can be increased.

As a result of an investigation made by the inventors, it has been found that, when a cell having a cell diameter 1.3 or more times the mode in the cell diameter distribution is selected as the cell to be processed, the cell 8 in a division process as shown in FIG. 3A can be efficiently collected. Accordingly, in the present disclosure, a cell group including cells in a proliferation process is used as the cell group for selecting the cell to be processed for being subjected to cell processing. In addition, the cell to be processed is preferably a cell, which is separated from the above-mentioned cell group, and which has a cell diameter 1.3 or more times the mode in the cell diameter distribution of the cell group.

In the introducing step (B), the cell suspension prepared in the preparing step (A) is passed through an orifice. Thus, by the above-mentioned mechanism, the cell membrane 4 is punctured, and the target substance 2 is introduced into the cell. A method of passing the cell suspension through an orifice is not particularly limited, and any method may be applied as long as the method is a technique for passing the cell suspension through an orifice forming member including an orifice as a shear force applying member.

In one exemplary embodiment, in the introducing step (B), the orifice is included in a liquid ejection head, and the target substance is introduced into the cell to be processed by ejecting the cell suspension from the orifice by the liquid ejection head. Therefore, the liquid ejection head corresponds to an orifice forming member. The kind of the liquid ejection head is not limited, and a liquid ejection head configured to perform inkjet by a piezoelectric system, or a liquid ejection head configured to perform inkjet by a thermal system may be used. Among physical introduction techniques, a method involving utilizing a liquid ejection head can inexpensively achieve cell processing and has a high cost advantage as compared to other physical introduction techniques.

Figure 4:
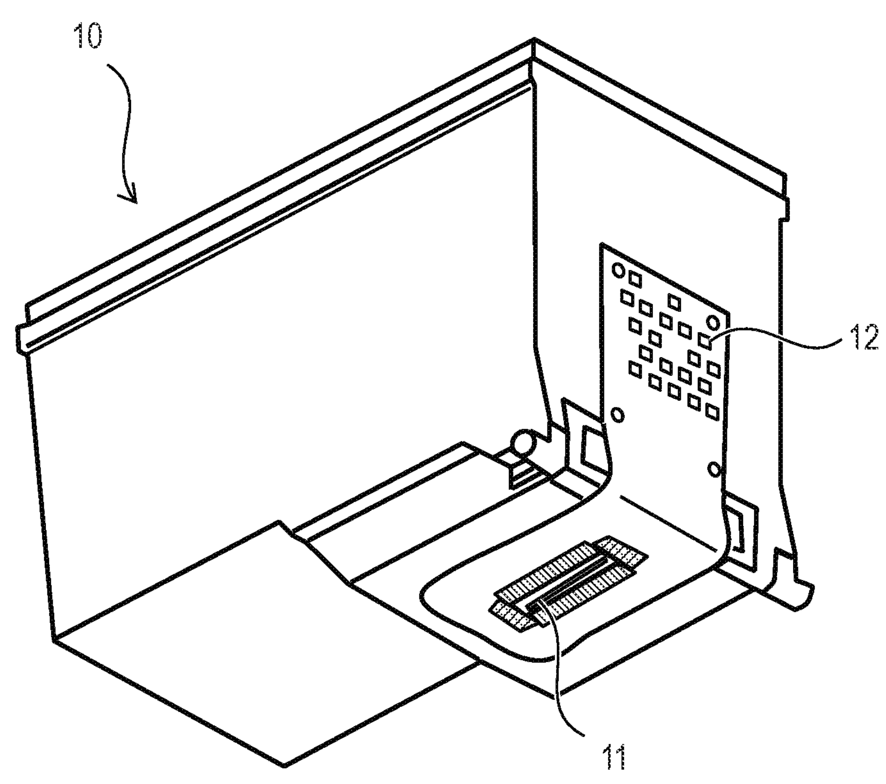
FIG. 4 is a schematic view for illustrating the exterior configuration of a liquid ejection head.
Figure 4:
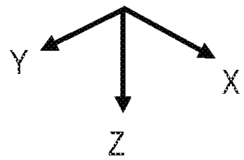

The exterior configuration of an example of the liquid ejection head configured to perform inkjet by the thermal system, which is suitably used in the present disclosure, is illustrated in FIG. 4. As illustrated in FIG. 4, a liquid ejection head 10 internally includes a substrate 11, an electrical connection portion 12 configured to send electric power or a signal to the substrate 11, and a space capable of storing a liquid to be ejected. In the following description, a direction parallel to a short side of the rectangular exterior of the substrate 11 is referred to as "X direction", a direction parallel to a long side of the rectangular exterior of the substrate 11 is referred to as "Y direction", and a direction perpendicular to the X direction and the Y direction is referred to as "Z direction". In addition, a direction going from the liquid ejection head 10 to the outside of the substrate 11 is defined as the + side of the Z direction.

Figure 5A:
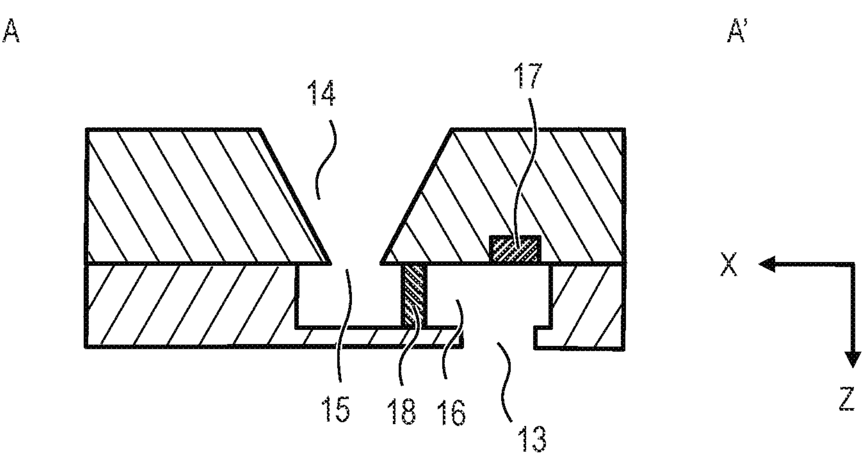
FIG. 5A is an enlarged view for illustrating a cross-section of a substrate included in the liquid ejection head parallel to an XZ plane.
Figure 5B:
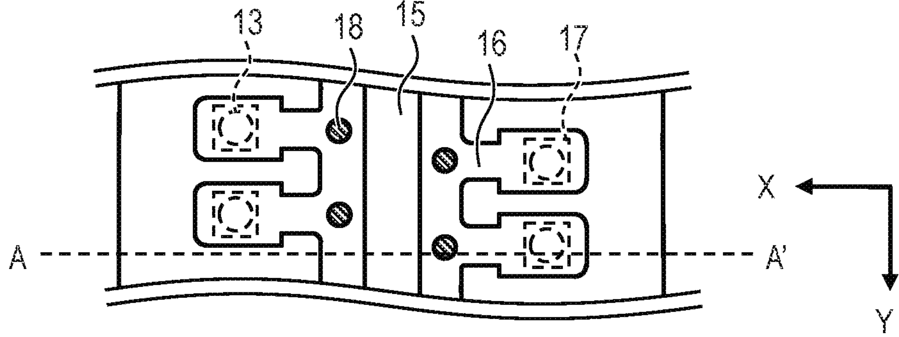
FIG. 5B is an enlarged perspective view of the substrate, for illustrating its internal structure around orifices of the substrate from a +Z perspective.

FIG. 5A is an enlarged view for illustrating a cross-section of the substrate 11 parallel to an XZ plane. In addition, FIG. 5B is an enlarged perspective view of the substrate 11, for illustrating its internal structure around orifices 13 of the substrate 11 from a +Z perspective. The cross-section illustrated in FIG. 5A corresponds to the position indicated by the line A-A' of FIG. 5B.

The substrate 11 includes a plurality of orifices 13, a common liquid chamber 14, a liquid supply port 15, a plurality of supply flow paths 16, and a heating element (electrothermal conversion element) 17. The plurality of orifices 13 are arranged by being arrayed in rows in the Y direction. The common liquid chamber 14 has a shape extending along the rows of the orifices 13, and is configured so that the cell suspension is supplied to each of the supply flow paths 16 while flowing from one end side of the rows of the orifices 13 to the other end side thereof. The liquid supply port 15 is an opening arranged in order to supply the cell suspension from the common liquid chamber 14 to the supply flow paths 16. The plurality of supply flow paths 16 are each configured to communicate the common liquid chamber 14 to a corresponding one of the orifices 13. The heating element 17 is configured to generate a pressure for ejecting the cell suspension. When the heating element 17 is energized for a short period of time, the liquid in the vicinity thereof is rapidly heated to cause bubbling, and the cell suspension passes through the orifices to be ejected. Further, the substrate 11 includes a nozzle filter 18 as a cell selecting member. The nozzle filter is preferably a pillar-shaped nozzle filter. The pillar-shaped nozzle filter has a pillar diameter "d", in a connection portion between the common liquid chamber 14 and each of the supply flow paths 16. As illustrated in FIG. 5B, the pillar-shaped nozzle filter 18 has a circular shape in a section parallel to an XY plane. The pillar diameter "d" is a diameter of the pillar-shaped nozzle filter 18 in the section parallel to the XY plane.

The cell suspension flowing in the common liquid chamber 14 can be generally loaded to reach the orifices 13 by wetting and spreading through surface tension. When the cell suspension is smoothly loaded to reach the orifices 13 by the wetting and spreading through surface tension, an introduction operation can be performed immediately after the loading. In those instances, when the loading does not reach the orifices 13 by the wetting and spreading through surface tension, a suction pump or the like is used to enable the loading by being pressed against the orifices 13 from the outside to perform suction. Alternatively, an external pressurization pump or the like is used to enable the loading by being communicated to the common liquid chamber 14 to pressurize a storage portion (not shown) configured to store the cell suspension.

It is appropriate that the ejected cell suspension be ejected onto a substrate or into a culture solution. A comprehensive load to be applied to the cells needs to be taken into consideration in selecting the substrate, and the substrate is selected in accordance with purposes. The cell suspension may be directly ejected from the liquid ejection head 10 onto a medium loaded in a culture dish, and a material for receiving the ejected cell suspension only needs to be selected in accordance with purposes.

All the nozzle filters 18 illustrated in FIG. 5B have the same pillar diameter "d", but the nozzle filters 18 may be configured to differ from each other in magnitude of the pillar diameter "d" in accordance with their arrangement positions.

Figure 6:
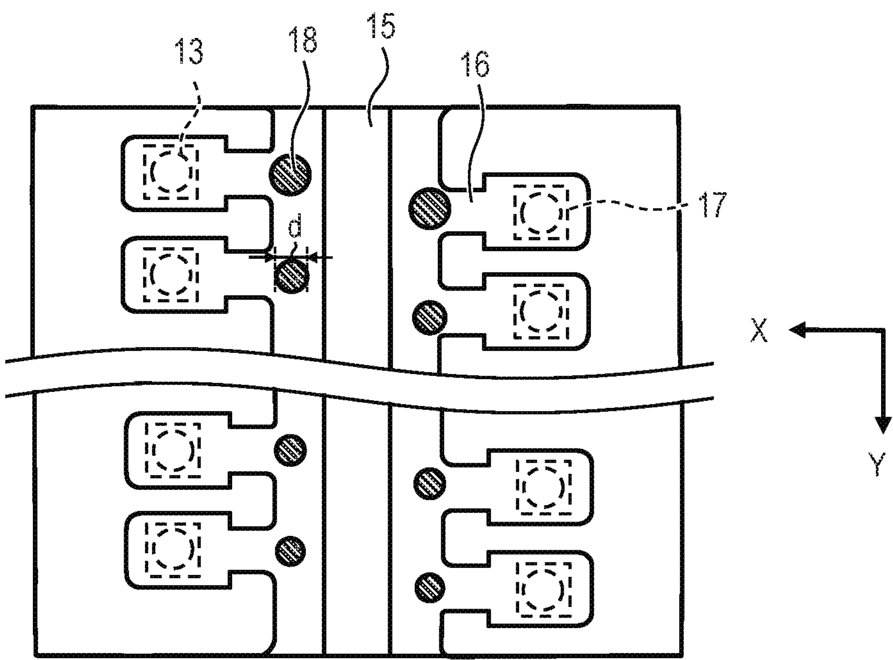
FIG. 6 is an enlarged perspective view of the substrate, for illustrating its internal structure around the orifices of the substrate from the +Z perspective.

FIG. 6 is an enlarged perspective view of the substrate 11, for illustrating its internal structure around the orifices 13 from the +Z perspective, in another example of the liquid ejection head configured to perform inkjet by the thermal system.

In the example illustrated in FIG. 6, the nozzle filters 18 have a smaller pillar diameter "d" on the downstream side (+Y side in FIG. 6) of the flow of liquid in the common liquid chamber 14 than on the upstream side (−Y side in FIG. 6) thereof. Further, the nozzle filters 18 have, on the most upstream side of the flow of liquid in the common liquid chamber 14, a pillar diameter "d" of such a size that the cell to be processed cannot be supplied to the supply flow paths 16. Therefore, the cell to be processed is not supplied to the supply flow 16. In addition, the nozzle filters 18 have, on the most downstream side of the flow of liquid in the common liquid chamber 14, a pillar diameter "d" of such a size that the cell to be processed can be supplied to the supply flow 16.

When the pillar diameters "d" of the nozzle filters 18 are set as in the example illustrated in FIG. 6, the cell to be processed can be selected from the above-mentioned cell group through use of the nozzle filters 18.

That is, the liquid to be supplied to the common liquid chamber 14 of the liquid ejection head 10 can be a mixed liquid containing a cell group including cells in a proliferation process, and the target substance. In this case, in the common liquid chamber 14, the mixed liquid is supplied to each of the supply flow paths 16 while flowing from one end side (−Y side in FIG. 6) of the rows of the orifices 13 to the other end side (+Y side in FIG. 6) thereof. Then, cells having smaller cell diameters among the cells contained in the mixed liquid are introduced into the supply flow paths 16 located on the upstream side (−Y side in FIG. 6) of the flow in the common liquid chamber 14. In addition, cells having larger cell diameters among the cells contained in the mixed liquid are introduced into the supply flow paths 16 located on the downstream side (+Y side in FIG. 6) of the flow in the common liquid chamber 14. In this case, on the most upstream side of the flow of the mixed liquid in the common liquid chamber 14, the nozzle filter 18 is configured to have a pillar diameter "d" such a size that the cell to be processed cannot be supplied to the supply flow path 16. Besides, on the most downstream side of the flow of the mixed liquid in the common liquid chamber 14, the nozzle filter 18 is configured to have a pillar diameter "d" such a size that the cell to be processed can be supplied to the supply flow path 16. Then, the liquid ejected from the orifice 13 corresponding to the supply flow path 16 located on the downstream side to which the cell to be processed has been supplied becomes a liquid containing the cell to be processed for which cell processing has been carried out. Preferably, the nozzle filters 18 have, on the most upstream side of the flow of liquid in the common liquid chamber 14, the pillar diameters "d" of such a size that cells smaller than a mode of the cell group or cells having a cell diameter same as the mode (that is, cells other than the cell to be processed in the cell group) can be supplied to the supply flow paths. The nozzle filters 18 are not necessarily provided on the most downstream side of the flow of liquid in the common liquid chamber 14.

In the example illustrated in FIG. 6, the pillar diameters "d" of the nozzle filters 18 may be gradually reduced toward the direction of the flow of the mixed liquid in the common liquid chamber 14, or may be rapidly reduced in a certain downstream region.

In addition, in the example illustrated in FIG. 6, the nozzle filters 18 illustrated are pillar-shaped. However, the shape of a cross-section of each of the nozzle filters 18 parallel to the XY plane is not limited to a circular shape. The shape of the cross-section of each of the nozzle filters 18 parallel to the XY plane may be any shape as long as the cell to be processed can be selected from the above-mentioned cell group by controlling the sizes of the flow paths narrowed by the nozzle filters 18.

For the determination of the introduction of the target substance into the cell to be processed in the cell processing, an optimal method only needs to be appropriately used in accordance with the kind of the target substance. Specifically, for example, when plasmid DNA (pDNA) or the like expressing a fluorescent protein GFP or RFP has been introduced into the cell to be processed, the introduction thereof may be determined as described below. That is, for cells after the passage of a certain period of time from the processing treatment, the presence or absence of light emission based on the fluorescent protein is determined using a fluorescence microscope. Thus, the amount of the target substance introduced can be semi-quantitatively determined. In addition, the number cells into each of which the target substance has been introduced can also be quantitatively determined in the following manner: cells cultured after the cell processing are monodispersed using an enzyme or the like as required, and then the number of cells emitting fluorescence is counted using flow cytometry or the like. In addition, after the processing treatment, the cells may be disrupted and measured for fluorescence with a fluorescence spectrophotometer, a luminometer, or the like. In addition, an ELISA method or immunostaining method involving using an antigen-antibody reaction may be used. In addition, DNA introduced into the cells and amplified DNA may be directly measured using a real-time PCR apparatus or the like. When the target substance is a labeling compound, analysis may be performed using a general analysis technique for analyzing the labeling compound.

In the present disclosure, the target substance to be used is not limited, and hence versatility for usable target substances is high. In addition, the cell to be used for processing is selected utilizing an inherent property of cells (increase in cell diameter in a division process), and hence the introduction of the target substance into the cell to be processed can be carried out without impairing the viability of the cell.

Constituent elements involved in the cell processing method according to the present disclosure are described below.

(Orifices)

The opening shape of each of the orifices is preferably a circular shape as illustrated in FIG. 5B, but orifices each having any shape may be selected and used. Examples of the opening shape of each of the orifices include an oval shape, a triangle, a rectangle, a square, a polygon, a star shape, and a shape having a protrusion.

The cell to be subjected to the introduction, the target substance to be introduced into the cell, and the like are described in detail below with illustrative description.

(Cell Type)

Examples of the cell to be processed to be used in the present disclosure include adherent/floating cells, spheroids (aggregated cells), and further, cell lines/primary cells, and mammalian cells/insect cells/plant cells/yeast cells.

(Cell Diameter)

The cells forming the cell group for selecting the cell to be processed are each measured for the length of its cell diameter before the selecting and processing of the cell to be processed are carried out. The cell diameter may be measured by preparing a liquid containing the cells, transferring the liquid to a hemocytometer or the like, and using, for example, an optical microscope mounted with an image sensor. Through use of an image recorded using the image sensor, the cell diameter may be determined in accordance with purposes based on distance information corresponding to an image stored in advance. It is preferred that the cells be brought into focus, and then an imaging image be recorded, followed by length measurement. When the cell diameters vary, the cell diameter distribution is developed into a histogram with classes at intervals of 1 μm, and the mode in the histogram is determined.

(Liquid for Preparing Cell Suspension)

A liquid for preparing the cell suspension is not particularly limited, but examples thereof include water, physiological saline, buffers, such as phosphate buffered saline (hereinafter referred to as "PBS") and Tris, various media, such as Dulbecco's Modified Eagle Medium (hereinafter referred to as "D-MEM"), Iscove's Modified Dulbecco's Medium (hereinafter referred to as "IMDM"), Hanks' Balanced Salt Solutions (hereinafter referred to as "HBSS"), Minimum Essential Medium-Eagle, Earle's Salts Base, with Non-Essential Amino Acid (hereinafter referred to as "MEM-NEAA"), Roswell Park Memorial Institute Medium (RPMI) 1640, and F-12, sera, commercially available buffers for electroporation, commercially available buffers for FACS analysis, and infusion solutions such as lactated Ringer's solution. Two or more kinds of those liquids may be used as a mixture. The water is preferably water that has been deionized by ion exchange or the like, and sterilized with an autoclave or the like.

The liquid for preparing the cell suspension may contain, for example, a salt, a saccharide, a ribonucleotide, a growth factor or a hormone, a pH buffering agent, a surfactant, a chelating agent, a water-soluble organic solvent, a protein, an amino acid, an antimicrobial agent, a moisturizing agent, and a thickener.

Examples of the salt include inorganic salts and organic salts to be used for cell culture. Specific examples of the salt include sodium chloride, potassium chloride, and sodium citrate.

As the saccharide, for example, glucose, sucrose, and fructose may be used for the purpose of, for example, supplying a nutrient to cells or adjusting an osmotic pressure.

As the ribonucleotide, for example, adenosine triphosphate, guanosine triphosphate, and the like may be used for the purpose of aiding cell metabolism.

Examples of the growth factor and the hormone include a human growth hormone, other animal growth hormones, such as a bovine growth factor, a porcine growth factor, and a chicken growth factor, insulin, oxytocin, angiotensin, methionine enkephalin, substance P, ET-1, FGF, KGF, EGF, IGF, PDGF, LHRH, GHRH, FSH, DDAVP, PTH, vasopressin, glucagon, and somatostatin.

Examples of the pH buffering agent include a citrate buffer, a phosphate buffer, a Tris buffer, and a HEPES buffer.

As the surfactant, for example, one kind or a plurality of kinds of anionic, cationic, amphoteric, and nonionic water-soluble surfactants may be used. However, the surfactant is preferably incorporated into the liquid in such an amount that the surface tension of the liquid becomes 25 mN/m or more.

Examples of the chelating agent include ethylenediaminetetraacetic acid (EDTA) and ethylene glycol tetraacetic acid (EGTA).

Examples of the water-soluble organic solvent include glycerin, polyethylene glycol, and dimethyl sulfoxide. In addition, the content of the water-soluble organic solvent in the cell suspension is preferably 0.001 mass % or more and 50 mass % or less with respect to the total mass of the cell suspension.

Examples of the protein include sera, such as fetal bovine serum (FBS) and horse serum.

Examples of the antimicrobial agent include sodium azide and an antibiotic such as penicillin-streptomycin (P/S).

Examples of the moisturizing agent include polyhydric alcohols, such as glycerin, propylene glycol, butylene glycol, and sorbit, mucopolysaccharides, such as hyaluronic acid and chondroitin sulfate, soluble collagen, and hydrolysates of proteins, such as elastin and keratin. Those moisturizing agents may be used alone or as a mixture thereof.

As the thickener, for example, a water-soluble polymer compound may be used. Examples of the water-soluble polymer compound include: starches, such as an oxidation-modified starch, an enzyme-modified starch, a thermochemically modified starch, a cationic starch, an amphoteric starch, and an esterified starch; cellulose derivatives, such as carboxymethyl cellulose, hydroxyethyl cellulose, and ethyl cellulose; natural or semi-synthetic polymers, such as casein, gelatin, and a soy protein; and polyvinyl alcohol and fully saponified or partially saponified products thereof, such as acetoacetylated polyvinyl alcohol, carboxy-modified polyvinyl alcohol, olefin-modified polyvinyl alcohol, and silyl-modified polyvinyl alcohol. Those water-soluble polymer compounds may be used alone or in combination thereof.

(Target Substance)

The target substance to be introduced may be appropriately selected in accordance with its purpose. Examples of the target substance include a nucleic acid, a protein, and a labeling substance, but the target substance is not limited thereto as long as the target substance has such a size as to be incorporated into the nucleus of the cell to be processed.

For the purpose of transiently and stably expressing a nucleic acid or interfering with a gene, an exogenous ribonucleic acid (RNA) and deoxyribonucleic acid (DNA) that are not derived from the cell to be processed may each be used as the target substance. As a higher-order structure that the nucleic acid may assume, there are given a single-stranded primary structural body, secondary structures, such as a hairpin-shaped stem-loop structure and a helix structure, and tertiary structures, such as A-Form, B-Form, and Z-Form. In addition, the nucleic acid may be labeled with a fluorescent compound or a radioisotope in accordance with purposes.

Examples of the RNA include: messenger RNA, which serves to copy and transport a sequence from DNA to a ribosome, which is an organelle for synthesizing a protein; ribosomal RNA, which is a constituent element of the ribosome; transfer RNA, which transfers an amino acid having a corresponding sequence to the ribosome; small nuclear RNA; small nucleolar RNA; microRNA; and siRNA having an interference action. However, suitable RNA may be used in accordance with purposes without being limited to the foregoing.

As the DNA, any of single-stranded DNA, double-stranded DNA, triple-stranded DNA, and quadruplex DNA may be selected and used. With regard to the shape of the DNA, a linear shape, a circular shape, or the like is generally used, but the DNA may have any shape such as DNA origami, which has been attracting attention in recent years, and the shape of the DNA is not particularly limited. Double-stranded DNA is preferred in terms of the stability of DNA, and circular plasmid DNA is more preferred in terms of the ease of amplification in *Escherichia coli* or yeast. Further, to be introduced into a cell, the DNA needs to be introduced from above the cell membrane into the inside of the cell, and hence preferably has as small a surface area as possible. For example, even among DNAs having identical sequences, circular DNA is preferred to linear DNA, and supercoiled DNA resulting from the twisting of DNA is more preferred.

(Protein)

The protein is preferably used by being dissolved, dispersed, or supported on a substrate and dispersed in order to be introduced into the cell suspension. Examples of the structure of the protein include: a primary structure including a polypeptide; secondary structures, such as an $\alpha$-helix and a $\beta$-sheet; a tertiary structure containing those secondary structures; and a quaternary structure such as hemoglobin. A protein having a higher-order structure in accordance with purposes may be used. Specific examples of the protein include enzyme proteins such as amylase, structural proteins, such as collagen and keratin, transport proteins such as albumin, storage proteins such as ferritin, contractile proteins, such as actin and myosin, protective proteins such as globulin, regulatory proteins such as calmodulin, other various membrane proteins, zinc finger nucleases for genome editing, and a Cas9 protein used for CRISPER/Cas9.

(Labeling Substance)

The labeling substance only needs to allow labeling to be recognized from the outside of cells after being introduced into the cells, and may be introduced into the cell to be processed by chemically or physically modifying a nucleic acid or a protein therewith. The labeling substance only needs to have such an absorption wavelength or fluorescence wavelength as to be recognizable separately from the cell to be processed. In addition, the labeling substance may be allowed to be present in a state of being dissolved or dispersed in the cell suspension, or in a state of being dispersed and supported on a substrate. Specific examples of the labeling substance include a stable isotope substance, such as deuterium, $^{13}C$, or $^{15}N$, a radioactive substance, a dye, a fluorescent dye, a pigment, a fluorescent pigment, quantum dots, nanodiamond, fullerene, a carbon nanosheet, and a carbon nanotube.

A specific, non-limiting example is described below of a process required before reaching the introduction of the target substance into the cell to be processed in the present disclosure.

First, cryopreserved cells are thawed, and the cells are dispersed in a medium and seeded in a culture dish. The number of cells to be seeded in the culture dish is preferably $1\times10^5$ cells or more and $1\times10^6$ cells or less. The culture dish having the cells seeded therein is cultured in a culture system of interest. Specifically, in the case of animal cells, the cells are preferably cultured in an incubator, which is kept under 37° C. and a saturated water vapor having a carbon dioxide concentration of 5%, for 72 hours. During the culture period, it is preferred that the proliferation state of the cells be determined as required, and the medium be changed at any timing. Then, the cells are sufficiently proliferated with the incubator. In the case of adherent cells, the cells can be proliferated until the ratio of cells covering the bottom surface of the dish (confluency) becomes 90% or more.

After that, the cells are separated from the culture dish, and a cell having a cell diameter 1.3 or more times the mode in the cell diameter distribution of the cell group is selected and used as the cell to be processed.

As an example of a technique for selecting the cell to be processed, when the cell group contains adherent cells, there is given a method involving utilizing a change in adherence of the adherent cells to the surface of a culture substrate in a culture process. The adherent cells enlarge their own diameters in the process of proliferation, and hence weaken their adherence to the culture dish. Through utilization of the weakening of the adherence, the cell to be processed can be collected by pouring a liquid over, and lightly washing, the bottom surface of the dish with a pipette without using, for example, trypsin, which is often used for detaching adherent cells.

In addition, as another technique for selecting the cell to be processed, there is given a method involving selecting the cell to be processed from the cell group through a mesh filter. In this case, a filter having an aperture smaller than the cell diameter of the cell to be processed is used as the mesh filter. The selection of the mesh filter can adapt to cells having various diameters, and hence can increase the degree of freedom.

After the cell to be processed has been selected from the cell group, the selected cell to be processed and the target substance are mixed with each other in a liquid, and the mixture is stirred using a pipette or a stirrer to prepare the cell suspension.

Subsequently, cell processing is carried out by passing the cell suspension through an orifice.

The processed cell is appropriately cultured in an appropriate environment in accordance with the kind of the cell used. Specifically, in the case of an animal cell, the cell is preferably cultured in an incubator kept under a culture temperature in Celsius of 37° C. and a saturated water vapor having a carbon dioxide concentration of 5%. During the culture, it is preferred that the proliferation state of cells be determined, and medium change or passage be carried out at any timing.

Example of the present disclosure is described in detail below. The present disclosure is not limited to Example described below, and various modifications may be made without departing from the gist of the present disclosure.

According to one aspect of the present disclosure, the cell processing method and the cell processing apparatus being highly versatile for usable target substances and highly efficient for introducing of a target substance into a cell can be provided.

EXAMPLES

Example 1

(Preparation of Cell Suspension)

Cells used were Chinese hamster ovary cells (CHO-K1), which were adherent cells. A cell group of the cryopreserved cells were dispersed in Ham's F-12 Nutrient Mix (F-12 medium), and then seeded in a culture dish and cultured in an incubator, which was kept under 37° C. and a saturated water vapor having a carbon dioxide concentration of 5%, for 72 hours. After the culture, F-12 medium was lightly poured onto the culture dish, which had become about 90% confluent, with a pipette, and cells with weakened adhesiveness were collected from the culture dish. The collected cells were used as cells to be processed. Thus, the cells to be processed were selected from the cell group. The cells to be processed had a larger cell diameter than a mode (12.0 μm) in the cell diameter distribution of the cell group before selecting the cell to be processed. And the cells to be processed had the cell diameter 1.3 or more times the mode in the cell diameter distribution of the cell group before selecting the cell to be processed. The resultant cells to be processed were re-dispersed in F-12 medium.

In addition, CMV-Fresno RFP (trade name: FPB-54-609, Cosmo Bio Co., Ltd.) (hereinafter referred to as "RFP-DNA"), which was DNA encoding a fluorescent protein, was prepared as a target substance.

The cells to be processed dispersed in the F-12 medium were mixed with RFP-DNA serving as the target substance to provide a cell suspension. The fluorescent protein to be expressed in the cells by introducing RFP-DNA had a fluorescence spectrum with an excitation wavelength (maximum) of 553 nm and a fluorescence wavelength (maximum) of 592 nm. The cell suspension was prepared so that the final concentration of the cells to be processed was $2.0\times10^6$ cells/ml, and the final concentration of RFP-DNA was 1.0 μg/μl.

(Introduction of Target Substance)

An inkjet printer (trade name: G1310, Canon Inc.) was used as a cell processing apparatus to be used for the introducing step. Through use of the cell processing apparatus, a liquid ejection operation for outputting a 1.5 cm×1.5 cm solid image was performed to eject the cell suspension from a liquid ejection head toward the culture dish, which was placed at a distance of 10 mm from an ejection surface. This liquid ejection operation was repeated 40 times.

The resolution in the output of the 1.5 cm×1.5 cm solid image was set to 600 dpi×600 dpi. That is, in the liquid ejection operation in the formation of the above-mentioned solid image, one dot, that is, one drop of the cell suspension was applied to a unit region of 1/600 inch×1/600 inch. In this Example, one drop of the cell suspension was 23.0 ng.

The total amount of cells to be ejected was preferably $1\times10^5$ cells or more and $1\times10^6$ cells or less, and in this Example, an amount falling within this range was adopted.

Under the above-mentioned conditions, the cell suspension was loaded into a printer head and ejected toward the culture dish. After the ejection, F-12 medium was added to the culture dish, and the cells were cultured in an incubator under an environment at 37° C. and 5% $CO_2$ for 24 hours.

(Evaluation)

Fluorescence observation was carried out in order to determine that RFP-DNA had been introduced into the cells to be processed. For the fluorescence observation, observation was performed using a fluorescence microscope (trade name: BZ-8000, KEYENCE). In the fluorescence observation, a 20% neutral density filter was mounted, and trade name: BZ-X Filter TRITC (excitation wavelength Ex: 540±12.5 nm, emission wavelength Em: 605±27.5 nm) (KEYENCE) was mounted as a fluorescence filter cube. In the acquisition of images through the fluorescence observation, two kinds, i.e., a bright-field image without through any fluorescence filter cube and a TRITC fluorescence image through the above-mentioned fluorescence filter cube were acquired. At this time, the ratio of the number of cells emitting fluorescence observed in the TRITC fluorescence image to the total number of cells observed in the bright-field image was evaluated as an introduction ratio of the target substance.

Example 2

In this Example 2, cells to be processed were not selected from the cell group as in the Example 1 described above, and the all cells included in the cell group were used as cells serving as processing targets.

(Preparation of Liquid to be Subjected to Cell Processing)

Cells used were CHO-K1. A cell group of the cryopreserved cells were dispersed in F-12 medium, and then seeded in a culture dish and cultured.

After the culture, trypsin was added to the culture dish, which had become about 90% confluent, to detach all cells adhering to the dish. The detached cells contained cells with a cell diameter smaller than a mode (12.0 μm) in the cell diameter distribution of the cell group after the culture. The detached cells were centrifuged, and the supernatant was collected and then redispersed in F-12 medium.

Further, RFP-DNA serving as the target substance was mixed with the dispersion, and the mixture was used as a liquid to be subjected to cell processing. The liquid to be subjected to cell processing was set to have a final concentration of the cells of $2.0\times10^6$ cells/ml and a concentration of RFP-DNA of 1.0 μg/μl.

The subsequent introducing step and evaluation were carried out in the same manner as in Example 1.

<Evaluation Results>

Figure 7:
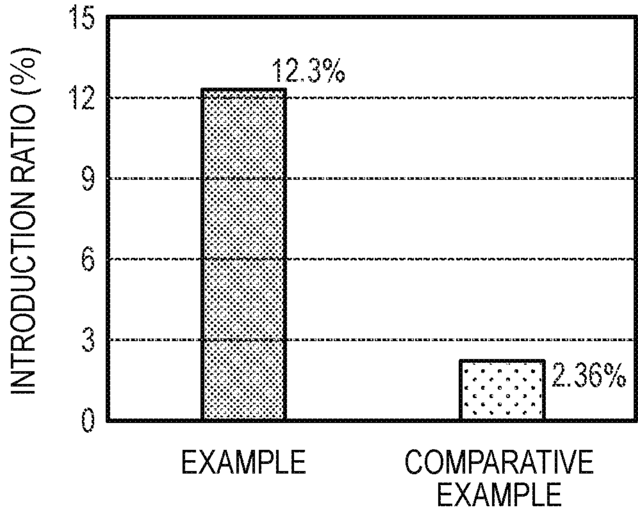
FIG. 7 is a graph showing the results of introduction ratios obtained in Example and Comparative Example.

The results of the introduction ratios of RFP-DNA in Example 1 and Example 2 are shown in FIG. 7. As shown in FIG. 7, the introduction ratio in Example 2 was 2.36%, whereas the introduction ratio in Example 1 was 12.3%, achieving a higher value than the introduction ratio in Example 2. In Example 1, the introduction ratio was about 5.1 times that in Example 2.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. A cell processing method comprising:

preparing a cell suspension containing a cell to be processed and a target substance, wherein the cell to be processed is a cell which is selected from a cell group including cells in a proliferation process, and which has a cell diameter larger than a mode in a cell diameter distribution of the cell group; and introducing the target substance into the cell to be processed by allowing a shear force to act on the cell to be processed, wherein allowing a shear force to act comprises ejecting the cell suspension from an orifice by a liquid injection head, wherein the orifice is included in the liquid ejection head;

wherein the liquid ejection head includes:

a plurality of the orifices arrayed in a row;

a common liquid chamber having a shape extending along the row of the orifices; and a plurality of supply flow paths each configured to communicate the common liquid chamber to a corresponding one of the orifices, wherein the common liquid chamber is configured so that a mixed liquid containing the cell group and the target substance is supplied to each of the supply flow paths while flowing from one end side of the row of the orifices to another end side thereof, wherein a connection portion between the common liquid chamber and each of the supply flow paths has arranged therein a pillar-shaped nozzle filter, wherein the nozzle filters have a smaller pillar diameter on a downstream side of a flow of the mixed liquid in the common liquid chamber than on an upstream side thereof, and have, on a most upstream side of the flow of the mixed liquid in the common liquid chamber, a pillar diameter of such a size that the cell to be processed cannot be supplied to a corresponding one of the supply flow paths, and have, on a most downstream side of the flow of the mixed liquid in the common liquid chamber, a pillar diameter of such a size that the cell to be processed can be supplied to a corresponding one of the supply flow paths, and wherein the cell to be processed is selected from the cell group through utilization of the nozzle filters.

2. The cell processing method according to claim 1, wherein the cell to be processed is a cell having a cell diameter 1.3 or more times the mode in the cell diameter distribution of the cell group.

3. The cell processing method according to claim 1, wherein the cell to be processed is a cell selected from the cell group that has been processed through a mesh filter.

4. The cell processing method according to claim 1, wherein the cell group contains adherent cells, and wherein the cell to be processed is a cell selected from the cell group through utilization of a change in adherence of the adherent cells to a surface of a culture substrate in a culture process.

5. The cell processing method according to claim 1, wherein the target substance is a nucleic acid.

6. The cell processing method according to claim 1, wherein the target substance is a protein.

7. The cell processing method according to claim 1, wherein the pillar diameters of the nozzle filters are gradually reduced toward the direction of the flow of the mixed liquid in the common liquid chamber.

* * * * *